(12) United States Patent
Escaich Ferrer et al.

(10) Patent No.: US 9,420,785 B2
(45) Date of Patent: Aug. 23, 2016

(54) **ATTRACTANT FOR FLIES OF THE SPECIES *DROSOPHILA SUZUKII***

(71) Applicant: BIOIBERICA, S.A., Barcelona (ES)

(72) Inventors: Josep Escaich Ferrer, Barcelona (ES); Anna Botta Català, Barcelona (ES); Manuel Carrión Rodriguez, Lloret de Mar (ES); Cándido Marín Garrido, Archena (ES); Núria Sierras Serra, Mataró (ES); Rafael Piñol Dastis, Barcelona (ES)

(73) Assignee: BIOIBERICA, S.A., Barcelona (ES)

( * ) Notice: Subject to any disclaimer, the term of this patent is extended or adjusted under 35 U.S.C. 154(b) by 0 days.

(21) Appl. No.: 14/738,270

(22) Filed: Jun. 12, 2015

(65) Prior Publication Data

US 2015/0366194 A1    Dec. 24, 2015

(30) Foreign Application Priority Data

Jun. 20, 2014    (ES) .................................. 201430934

(51) Int. Cl.
*A01N 37/44* (2006.01)
*A01N 61/00* (2006.01)

(52) U.S. Cl.
CPC ................ *A01N 37/44* (2013.01); *A01N 61/00* (2013.01)

(58) Field of Classification Search
CPC .............................. A01N 61/00; A01N 37/44
USPC ........................................................ 424/77
See application file for complete search history.

(56) References Cited

U.S. PATENT DOCUMENTS

| 4,849,216 A | 7/1989 | Andersen |
| 2004/0208953 A1 | 10/2004 | Heath |

FOREIGN PATENT DOCUMENTS

| ES | 2293815 A1 | 3/2008 |
| WO | 99/22596 A1 | 5/1999 |
| WO | 2011018739 A2 | 2/2011 |

OTHER PUBLICATIONS

IAEA ("International Atomic Energy Agency"), Title: Trapping guidelines for area-wide fruit fly programs, issued 2003.*
Landolt, et al.; Title: Trapping spotted wing drosophila, *Drosophila suzukii* (Matsumura) (Diptera: Drosophilidae), with combinations of vinegar and wine, and acetic acid and ethanol, Journal of Applied Entomology, vol. 136 Issue 1-2, pp. 148-154. article first published online: Jun. 15, 2011.*
Mohammad et al., title: Process for Production of Hydrolysed Collagen from Agriculture Resources: Potential for Further Development; Journal of Applied Sciences, vol. 14, pp. 1319-1323; Published Apr. 11, 2014.*
Spanish Search Report dated Jun. 20, 2014, ES Application No. 201430934, 1 page.

* cited by examiner

*Primary Examiner* — Johann R Richter
*Assistant Examiner* — Yanzhi Zhang
(74) *Attorney, Agent, or Firm* — Rothwell, Figg, Ernst & Manbeck P.C.

(57) ABSTRACT

The present invention is related to the use of compositions comprising an enzymatic hydrolysate of animal cartilage protein, at least one organic acid from an alcoholic fermentation, and water, as attractant for flies of the species *Drosophila suzukii*. Preferably, the animal cartilage is bovine and/or porcine cartilage and the organic acid from an alcoholic fermentation is wine vinegar, apple cider vinegar, white vinegar or rice vinegar.

20 Claims, 5 Drawing Sheets

ACV = Apple cider vinegar
WV = Wine Vinegar

CSL = Corn Steep Liquor
ACV = Apple cider vinegar

CSL = Corn Steep Liquor
ACV = Apple cider vinegar

ACV = Apple cider vinegar

EPH = Enzymatic Protein Hydrolysate
ACV = Apple cider vinegar

ATTRACTANT FOR FLIES OF THE SPECIES *DROSOPHILA SUZUKII*

CROSS-REFERENCE TO RELATED APPLICATIONS

The present application is related to and claims priority to Spanish Application No. P 201430934, filed 20 Jun. 2014. This application is incorporated herein in its entirety.

TECHNICAL FIELD OF THE INVENTION

The present invention is related to the use of a composition as attractant for flies of the species *Drosophila suzukii*.

STATE OF THE PRIOR ART

The fly *Drosophila suzukii* (Matsumura, 1931) (Diptera Drosophilidae), also called Spotted Wing Drosophila, causes great economic losses in the fruit sector. It is a highly polyphagous invasive pest, endemic in Southeast Asia, which has recently been spreading to western countries like the United States, Canada, Mexico and several European countries (Cini et al., *Bulletin of Insectology* 65 (1), 149-160 (2012)). Its main hosts are soft fruits such as cherries, grapes, plums, strawberries and other cultivated berries, as well as wild berries and figs that serve as a reservoir when there is no susceptible crop. Indeed, the existence of alternative hosts that ripen at different times throughout the year exacerbates the potential pest status (Walsh et al., *Journal of Integrated Pest Management* 1, 1-7 (2011)). In addition to its wide range of hosts, *Drosophila suzukii* represents a significant threat to fruit farms due to its extreme fecundity and high dispersal potential (Cini et al., *Bulletin of Insectology* 65 (1), 149-160 (2012)). Unlike other flies that prefer rotten or fermented fruit, *Drosophila suzukii* attacks fresh ripe fruit. It is most active at 20° C and its activity is reduced at temperatures below 0° C. and above 30° C. (Walsh et al., *Journal of Integrated Pest Management* 1, 1-7 (2011)). In general, they prefer a moderate climate (although adults can endure long periods of cold); they are nevertheless very sensitive to desiccation. In our Mediterranean climate, the periods of greatest risk are concentrated especially in spring and autumn. This new pest is causing great concern since until now there was no efficient monitoring or control tool available for this species. Understanding their biology, ecology and distribution is essential for the development of control strategies compatible with integrated pest management. Following the indications of the European Union, alternatives to conventional insecticides have been developed in recent years. One of the alternatives is the use of apple cider vinegar as an attractant in traps. The effectiveness of a mixture of vinegar and wine has been described (P.J. Landolt et al. *J. AppL Entomol.* 136, 148-154 (2012)), even that of fruit extracts, for example, melon extract (patent application WO 2013/156492).

All this shows that there is a need for an alternative composition for use as an attractant (bait) of flies of the species *Drosophila suzukii*.

EXPLANATION OF THE INVENTION

The present inventors have found that, surprisingly, the compositions of the present invention exhibit a significant attractant effect of flies of the species *Drosophila suzukii*, wherein said effect is synergistic. Moreover, said compositions have been found to be highly specific for the fly *Drosophila suzukii*, capturing fewer *Drosophila* of other species. They have also found that the effectiveness and specificity of attractant compositions of the present invention are superior to those of other attractants.

Therefore, the present invention is related to the use of a composition comprising an enzymatic hydrolysate of animal cartilage protein, at least one organic acid from an alcoholic fermentation, and water, as attractant for flies of the species *Drosophila suzukii*.

In a preferred embodiment the animal cartilage is bovine and/or porcine cartilage.

In another preferred embodiment the organic acid from an alcoholic fermentation is selected from the group consisting of wine vinegar, apple cider vinegar, white vinegar and rice vinegar. Preferably, the organic acid is apple cider vinegar.

In a more preferred embodiment the enzymatic hydrolysate of animal cartilage protein has a degree of hydrolysis comprised between 8% and 30%. Preferably, the degree of hydrolysis is 20%.

In an equally preferred embodiment the enzymatic hydrolysate of animal cartilage protein has an average molecular weight less than or equal to 20,000 Daltons.

In another preferred embodiment the enzymatic hydrolysate of animal cartilage protein is in a concentration of between 300 g/L and 1,000 g/L.

In an equally preferred embodiment the organic acid is in a concentration of between 200 g/L and 600 g/L.

Preferably, the enzymatic hydrolysate of animal cartilage protein is in a concentration of 680 g/L and the organic acid is in a concentration of 340 g/L.

In a specially preferred embodiment the composition contains 2% by weight of acetic acid, relative to the total weight of the composition.

In another specially preferred embodiment the composition contains 7% by weight of enzymatic hydrolysate of animal cartilage protein, relative to the total weight of the composition.

Preferably the composition is placed in a container or trap containing openings making it easy for the fly to enter, and difficult for it to get out.

A composition of the invention to be used as attractant for *Drosophila suzukii* flies can be obtained from animal cartilage tissue, for example, bovine and/or porcine trachea, which is digested with a proteolytic enzyme, for example alcalase, at a temperature of 58° C.-60° C. and at a pH between 7.7 and 8.6. Then the enzyme is inactivated by heating, filtered, and the resulting solution is ultrafiltered. Once ultrafiltered, the resulting aqueous solution can be atomized to obtain a solid or it can be used directly, by mixing it with an organic acid from an alcoholic fermentation, for example wine vinegar, apple cider vinegar, white vinegar, rice vinegar or mixtures thereof and adding more water. The attractant composition thus prepared can be used directly or a preservative can be added to it such as for example sodium benzoate, potassium benzoate, calcium benzoate, sodium sorbate, potassium sorbate, calcium sorbate, propionic acid, methylparaben or propylparaben. Sodium benzoate is most preferred. The most preferred composition of the invention is the one comprising hydrolysate of bovine and/or porcine cartilage protein, apple cider vinegar, sodium benzoate and water.

In very hot climates, additives can be added to a composition of the invention in order to reduce the evaporation (for example propylene glycol).

In order to use a composition of the invention as attractant for *Drosophila suzukii* flies, it is introduced into a container or trap for flies. Any commercial trap can be used, being more effective those containing openings which make it easy for the fly to enter, and difficult for it to get out, whereby the fly is attracted to the trap due to the attractant, comes in and since it is unable to escape, it dies of exhaustion or by drowning in the liquid, since the compositions of the invention do not contain insecticides.

Also, a membrane impregnated with a composition of the invention can be provided within the trap for a slower release of the attractant.

The traps are hung at the level of the crop, spaced at least 25 cm from the ground, taking care that there are not branches with leaves clogging the entrance to the trap. The placement density of the traps per hectare depends, among others, on the total area of the plot, climate, type of crop to be protected, stage of the program and type of trap used. For example, about 200 traps can be used per hectare, reinforcing the perimeters and the wetter areas.

The filling of the traps can be carried out, for example, by means of a backpack, introducing the nozzle of the backpack through one of the holes, and when necessary, various refills can be carried out during the campaign. The period of time required for the replenishment of the attractant liquid can vary according to the temperature, degree of sun exposure and type of trap used.

The amount of attractant composition to be used will depend on the type of trap.

The compositions of the invention, which attract the fly *Drosophila suzukii*, can be used both for monitoring and for the mass capture of populations in crops susceptible to this pest.

The compositions of the invention have the advantage of not containing pheromones or insecticides. Nor is it necessary to add insecticides in its further use in the field, which ensures that environmental pollution is almost nil.

Moreover, they are stable and transparent compositions that can be used without generating precipitates or mucilage that could compromise the effectiveness and hinder the counting of the flies.

Another advantage is that the compositions used in the invention exhibit greater efficiency in the field as attractants for the fly *Drosophila suzukii*, compared to other attractants. It is worth noting that they are more effective than different types and dilutions of vinegar and than a protein hydrolysate from porcine intestinal mucosa.

Another advantage lies in the fact that the compositions used in the present invention have a high specificity in the capture of *Drosophila suzukii*, capturing fewer *Drosophila* of other species. In the studies of specificity, it should be noted the high percentage of specificity of a composition of the invention compared to the low percentage of specificity of apple cider vinegar.

Another additional advantage of the compositions of the present invention is that they have synergy of action. The mean captures of a composition of the invention was greater than the sum of the mean captures of the individual components.

DETAILED DESCRIPTION OF THE PREFERRED EMBODIMENTS

The following examples are merely illustrative and do not represent a limitation of the scope of the present invention.

EXAMPLE 1

Preparation of a Composition of the Invention Intended for use as Attractant for Flies of the Species *Drosophila suzukii*

432 kg of porcine and bovine trachea and 480 L of water were placed in a reactor. The mixture was heated at 58° C.-60° C. and the pH was adjusted between 7.7 and 8.6. After adjusting the pH, 6.5 L of alcalase were added, divided into five additions. The digestion was carried out for 12 hours. Then the pH was adjusted to 5.5-6.5 and heated at 87° C.-93° C. It was filtered, and the resulting aqueous solution was ultrafiltered to yield 666 L of aqueous solution of enzymatic protein hydrolysate from porcine and bovine cartilage. To prepare 1,000 L of the attractant composition, 666 L of aqueous solution of enzymatic protein hydrolysate from porcine and bovine cartilage were mixed with 334 L of apple cider vinegar of 5° acidity. Then 2 kg of sodium benzoate were added. The resulting composition of the invention had 2° acidity, a concentration of enzymatic protein hydrolysate from porcine and bovine cartilage of 680 g/L and a concentration of apple cider vinegar of 340 g/L.

EXAMPLE 2

Study of the Field Efficiency of a Composition of the Invention for the Fly Drosophila suzukii. Comparison with the Commercial Attractants Cera Trap (protein hydrolysate) and Torula (Yeast Bait) used for the Capture of Fruit Flies such as Ceratitis capitata The study was carried out in the municipality of Céret (France) on cherry trees. The attractant composition of Example 1 was used, and the comparison was carried out with two attractants used in the capture of other type of flies. There were three replicates per treatment with weekly assessments and rotation of the traps for a period of 3 weeks.

Results

Figure 1:
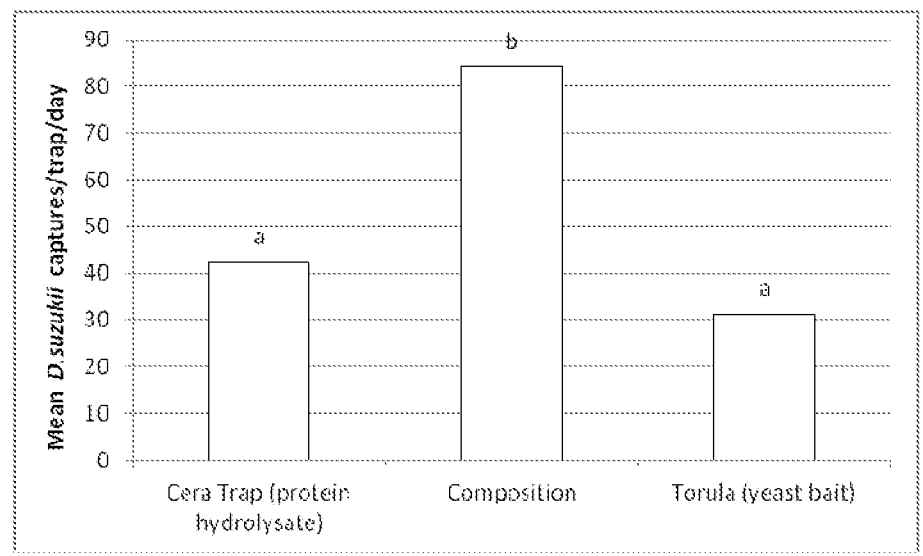
FIG. 1: This graph shows the comparison of the field efficiency against the fly *Drosophila suzukii* (No. of captured flies/trap/day) of the composition of the invention and the commercial attractants Cera Trap (protein hydrolysate) and Torula (yeast bait). Different letters mean significant differences with a significance level $P<0.05$ (LSD Test).

According to this study, the protein hydrolysate or the yeast bait, used for the capture of other fruit flies (Ceratitis capitata), can also capture the fly Drosophila suzukii, however, the composition of the invention shows a significantly higher efficiency for the capture of this particular fly. As shown in FIG. 1, when using the composition of the invention an average of 84 Drosophila suzukii flies/trap/day were captured, while the number of captures dropped to 42 Drosophila suzukii flies/trap/day for the protein hydrolysate Cera Trap and to 31 Drosophila suzukii flies/trap/day for the Torula yeast bait.

The result obtained with the protein hydrolysate Cera Trap is especially relevant, since, although said protein hydrolysate is different from the enzymatic hydrolysate of animal cartilage protein, which is one of the components of the compositions of the invention, said result shows that the increased efficiency of the composition of the invention is due to the combination of the enzymatic hydrolysate of animal cartilage protein with the organic acid from an alcoholic fermentation.

EXAMPLE 3

Study of the Field Efficiency of a Composition of the Invention for the Fly Drosophila suzukii. Comparison with Different Types and Dilutions of Vinegar The study was carried out in the municipality of Calella (Barcelona) on strawberry variety Albion. Traps were placed at the level of the crop, with four replicates per treatment and the male and female Drosophila suzukii captures were counted weekly and the rotation of the traps was carried out to avoid the position effect. Each fly trap was filled with 300 mL of the attractant product to be studied. The composition of the invention of Example 1 was compared to the different vinegars.

Results

Figure 2:
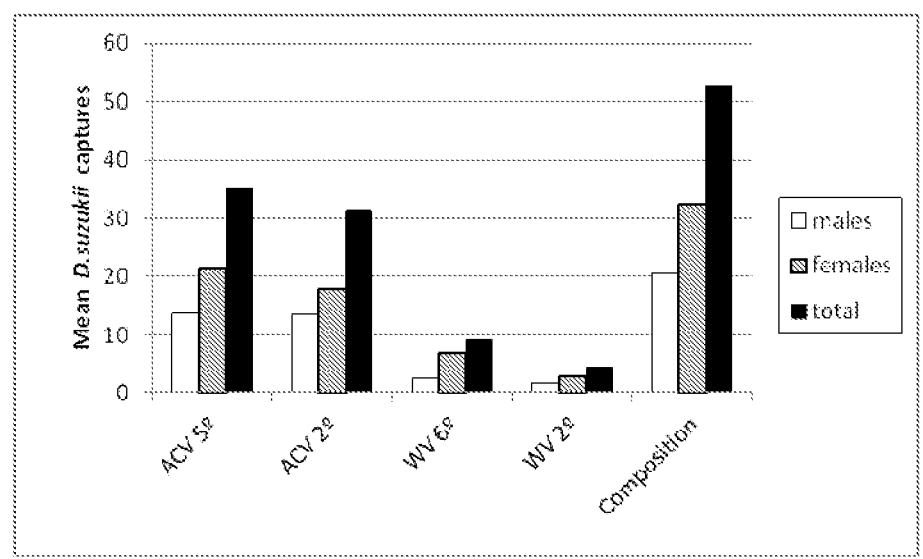
FIG. 2: This graph shows the comparison of the field efficiency against the fly *Drosophila suzukii* (mean captures in the period from Jul. 3 to Jul. 31) of the composition of the invention and different types and dilutions of vinegar. The captures of males, females and total are displayed.

FIG. 2 shows how the composition of the invention has higher Drosophila suzukii captures against the different types and dilutions of vinegar. It also has higher captures than the same water dilution of apple cider vinegar 2° of its composition (52.75 versus 31.5), which demonstrates the advantages of the combination of organic acid from an alcoholic fermentation, which in this particular case is the apple cider vinegar, with the enzymatic hydrolysate of animal cartilage protein.

EXAMPLE 4

Study of the Field Efficiency of a Composition of the Invention for the Fly Drosophila suzukii: Comparison with the Attractants Apple Cider Vinegar and Dros'Attract The aim of the study was to compare a composition of the invention (composition of Example 1) with two attractants used in the capture of Drosophila suzukii, the Apple cider vinegar and the commercial attractant Dros'Attract (composed of apple cider vinegar, wine must and sugar).

The test was carried out in Calella (Maresme) on strawberry variety Albion. The traps were placed at the level of the crop on Aug. 31, with four replicates per attractant and weekly rotation of the traps. Each trap was filled with 300 mL of the attractant product to be studied, and on Oct. 12 there was a replenishment of all the attractants.

Results

Figure 3:
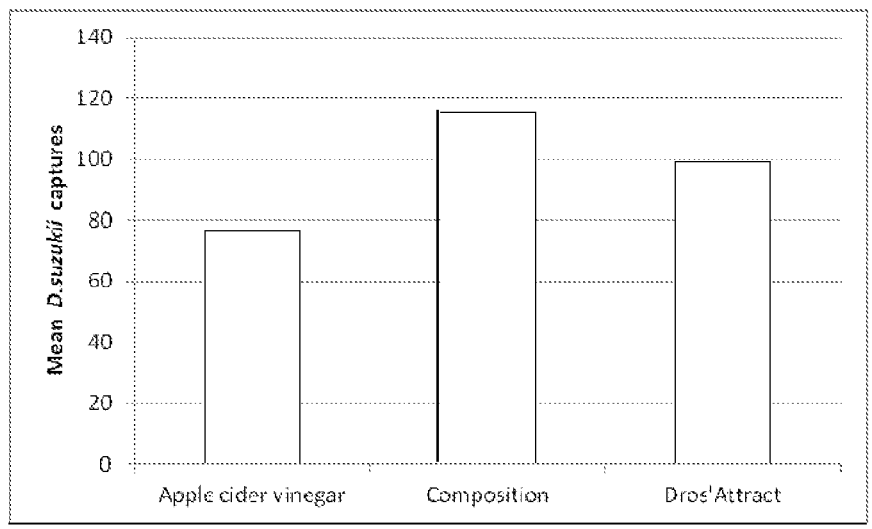
FIG. 3: This graph shows the comparison of the field efficiency against the fly *Drosophila suzukii* (mean captures in the period from Aug. 31 to Dec. 12) of the composition of the invention and the attractants Apple cider vinegar and Dros'Attract.

As shown in FIG. 3, this study showed once again that the attractant effectiveness of the composition of the invention is greater than that of the other attractants (Apple cider vinegar and Dros'Attract). It should be noted that the apple cider vinegar is the same that was used in the preparation of the composition of the invention; therefore it becomes apparent again that when combining the apple cider vinegar with the enzymatic hydrolysate of animal cartilage protein, the resulting composition shows greater efficiency.

EXAMPLE 5

Study of the Field Efficiency of a Composition of the Invention for the Fly Drosophila suzukii. Comparison with Different Attractants for Fruit Flies The aim of the study was to compare the efficiency of a composition of the invention (composition of Example 1) with different attractants used to capture other fruit flies. It was also compared again with the Apple cider vinegar, reference attractant in the capture of Drosophila suzukii.

The study was carried out in Whatcom County (Washington, USA) on raspberry. The traps were placed in field on Jun. 3 and were monitored weekly for male and female Drosophila suzukii captures until the end of the raspberry harvest (beginning of Aug.).

Results

Figure 4:
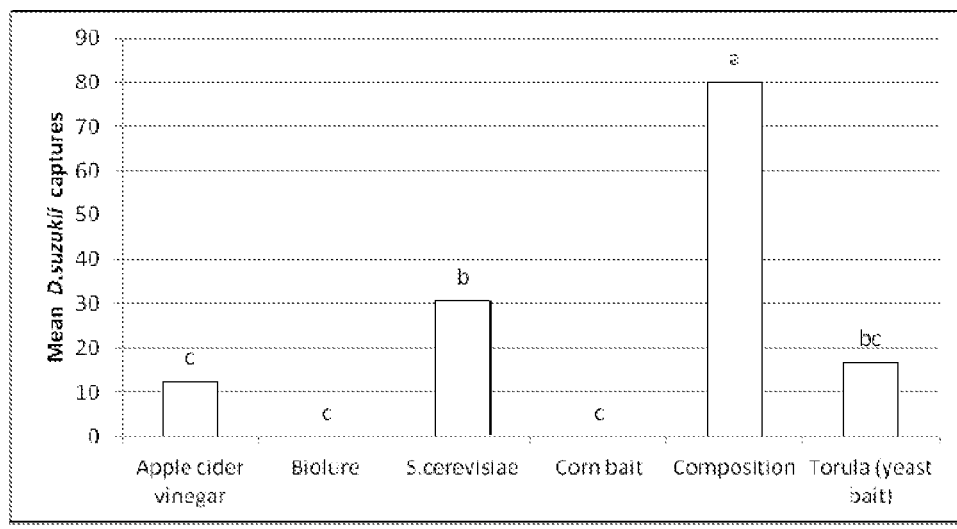
FIG. 4: This graph shows the comparison of the field efficiency against the fly *Drosophila suzukii* (mean captures in the period from Jun. 10 to Aug. 5) of the composition of the invention and the attractants Apple cider vinegar, Biolure, Baker's yeast (*S. cerevisiae*), Corn bait and Torula (yeast bait). Different letters mean significant differences with a significance level $P<0.05$ (LSD Test).

As shown in FIG. 4, the composition of the invention proved to be the best attractant for the capture of Drosophila suzukii, since the mean captures shown (80 flies) widely outperformed the other attractants studied. It should be noted that the attractants Biolure (composed of a mixture of ammonium acetate, putrescine and trimethylamine) and Corn bait did not manage to capture this kind of flies.

EXAMPLE 6

Study of the Field Efficiency of a Composition of the Invention for the Fly *Drosophila suzukii*. Comparison with the Attractant Solutions Apple Cider Vinegar and the Formula Corn Steep Liquor+Apple Cider Vinegar+Merlot Red Wine (1:0.75:0.75 CSL:ACV:Merlot The study was carried out in Stanislaus County (California, USA) on *Citrus reticulata*, Blank: 'W.Murcott Afourer'. Three replicates per treatment were prepared, in a randomized block design, with weekly assessment of captures and rotation of the traps.

Results

Figure 5:
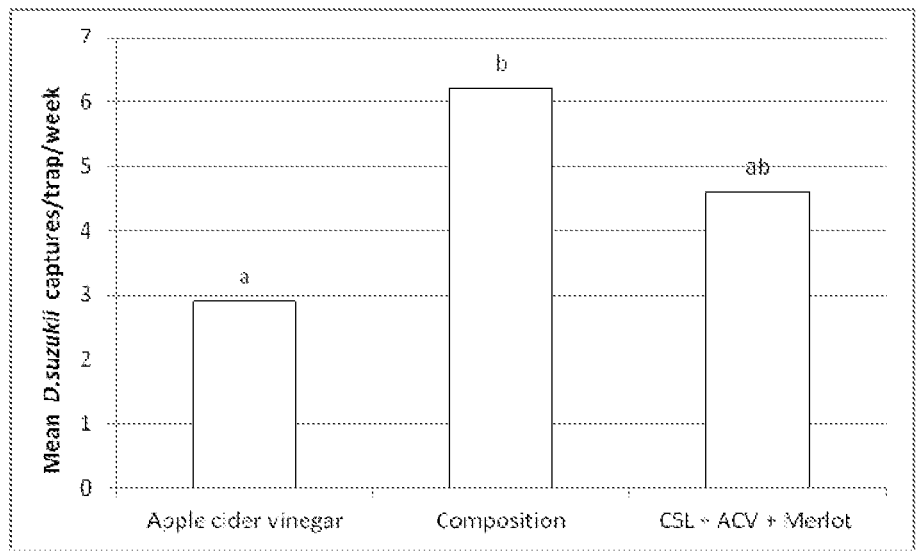
FIG. 5: This graph shows the comparison of the field efficiency against the fly *Drosophila suzukii* (mean No. of captured flies/trap/week) of the composition of the invention, the attractant Apple cider vinegar and the formula Corn steep liquor+Apple cider vinegar+Merlot red wine (1:0.75:0.75 CSL:ACV:Merlot). Different letters mean significant differences with a significance level $P<0.05$ (LSD Test).

FIG. 5 shows how the composition of the invention (composition of Example 1) stands out significantly over the Apple cider vinegar solution with regards to the attractant power against the fly *Drosophila suzukii* (6.2 flies/trap/week versus 2.9 flies/trap/week). The addition of Corn steep liquor and the Red wine to the Apple cider vinegar improved the attractant power (4.6 flies/trap/week), but the composition of the invention remained more attractant (6.2 flies/trap/week).

EXAMPLE 7

Study of the Specificity in the Capture of *Drosophila suzukii* in Field of a Composition of the Invention. Comparison with the Attractant Solutions Apple Cider Vinegar and the Formula Corn Steep Liquor+Apple Cider Vinegar+Merlot Red Wine (1:0.75:0.75 CSL:ACV:Merlot)

The study was carried out in Stanislaus County (California, USA) on *Citrus reticulata*, Blank: 'W.Murcott Afourer'. Three replicates per treatment were prepared, in a randomized block design, with weekly assessment of captures and rotation of the traps.

Results

Figure 6:
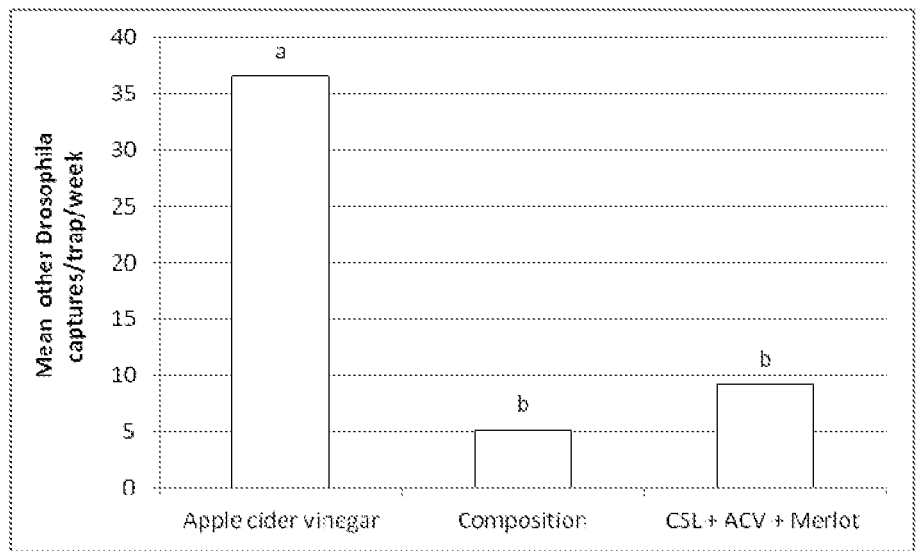
FIG. 6: This graph shows the comparison of the field specificity of the composition of the invention in the capture of *Drosophila suzukii*, the attractant Apple cider vinegar and the formula Corn steep liquor+Apple cider vinegar+Merlot red wine (1:0.75:0.75 CSL:ACV:Merlot). For this, the mean No. of captures of other *Drosophila* flies/trap/week is depicted for each attractant. Different letters mean significant differences with a significance level $P<0.05$ (LSD Test).

FIG. 6 shows how the composition of the invention (composition of Example 1) captures fewer *Drosophila* from other species, being very specific for the pest fly *Drosophila suzukii*. The specificity percentage of the composition of the invention is 54%, against 7% of Apple cider vinegar and 33% of the combination CSL+ACV+Merlot in this test.

EXAMPLE 8

Study of the Specificity in the Capture of *Drosophila suzukii* in field of a Composition of the Invention. Comparison with the Attractant Solution Whole Wheat Bait+Apple Cider Vinegar The study was carried out in the state of Connecticut (USA) on vine. 2×2 factorial experimental design, with 6 replicates per treatment for one week.

The composition of the invention of Example 1 was used.

Results

Figure 7:
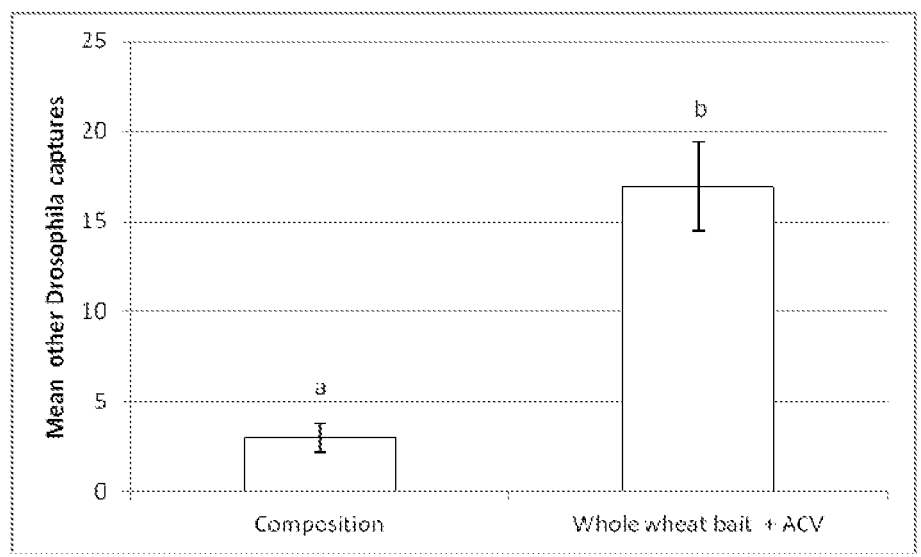
FIG. 7: This graph shows the comparison of the specificity in the capture of *Drosophila suzukii* in vine field of the composition of the invention and the attractant Whole wheat bait+Apple cider vinegar. For this, the mean captures of other *Drosophila* flies are depicted for each attractant. Different letters mean significant differences with a significance level $P<0.05$ (LSD Test).

As shown in FIG. 7, the composition of the invention proved to be a highly specific attractant solution for the capture of *Drosophila suzukii*, since the capture of other *Drosophila* was significantly lower than that of the Whole wheat bait+Apple cider vinegar (Whole wheat bait+ACV) attractant. The specificity percentage in the capture of *Drosophila suzukii* relative to the total captures of *Drosophila* sp. was 87% for the composition of the invention against 56% of the Whole wheat bait+ACV attractant.

EXAMPLE 9

Study of the Specificity in the Capture of *Drosophila suzukii* in Field of a Composition of the Invention. Comparison with the Cherry Wine Attractant Solution The study was carried out in Sant Pol de Mar (Barcelona) on strawberry variety Amandine. Three replicates per treatment were prepared, with weekly assessment and rotation of the traps for one month.

Results

Figure 8:
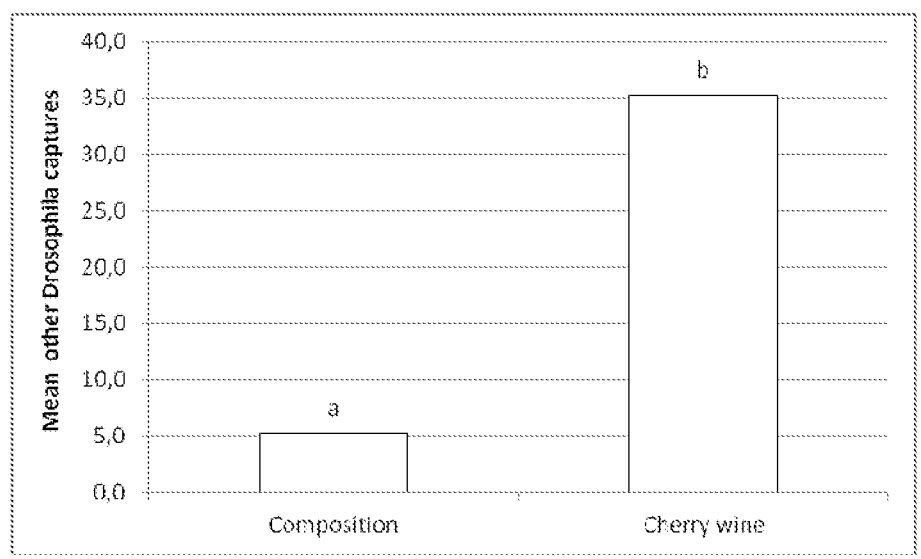
FIG. 8: This graph shows the comparison of the specificity in the capture of *Drosophila suzukii* in strawberry field of the composition of the invention and Cherry wine. For this, the mean captures of other *Drosophila* are depicted for each attractant. Different letters mean significant differences with a significance level $P<0.05$ (LSD Test).

As shown in FIG. 8, the composition of the invention (composition of Example 1) proved to be a highly specific attractant solution for *Drosophila suzukii*, since the capture of other *Drosophila* was significantly lower with respect to the capture with Cherry wine. The specificity percentage in the capture of *D.suzukii* with respect to the total captures of *Drosophila* sp. of the composition of the invention was 94% with respect to 76% of Cherry wine.

EXAMPLE 10

Study of Efficiency and Synergy of a Composition of the Invention for the Fly *Drosophila suzukii*. Comparison of the Composition with its Individual Components Enzymatic Protein Hydrolysate and Apple Cider Vinegar The study was carried out in Sant Pol de Mar (Maresme) on strawberry variety Albion. The traps were placed in field on Sep. 19, with 3 replicates per attractant and weekly rotation of the traps for one month, such that all the replicates went through all the positions. Each trap was filled with 600 mL of a composition of the invention containing 66% Enzymatic protein hydrolysate and 34% Apple cider vinegar or the individual component (66% Enzymatic protein hydrolysates or 34% Apple cider vinegar).

Results

Figure 9:
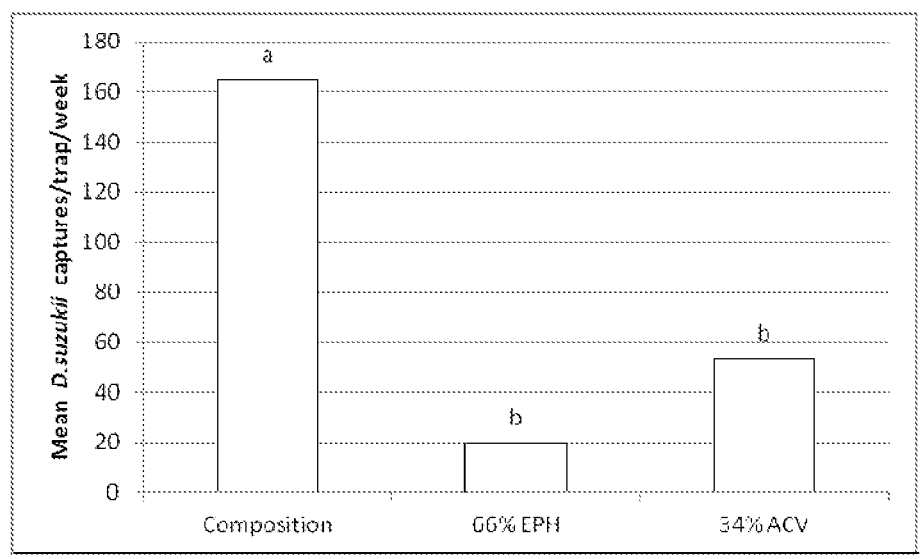
FIG. 9: This graph shows the comparison of the effectiveness in the capture of *Drosophila suzukii* (mean captures/trap/week) of the composition of the invention and its individual components: 66% Enzymatic protein hydrolysate (66% EPH) and 34% Apple cider vinegar (34% ACV) at the proportion of the composition. Different letters mean significant differences with a significance level $P<0.05$ (LSD Test).

According to this study, the composition of the invention showed a statistically significant greater efficiency (LSD Test, $\alpha=0.05$) in the capture of *Drosophila suzukii* compared to its individual components 66% Enzymatic protein hydrolysate and 34% Apple cider vinegar, and also a synergistic effect was observed, since the mean captures of the composition of the invention was greater than the sum of the mean captures of the individual components (FIG. 9).

What is claimed is:

1. A method of attracting flies of the species *Drosophila suzukii* comprising providing an attractant composition comprising an enzymatic hydrolysate of animal cartilage protein, at least one organic acid from an alcoholic fermentation and water in a field where the flies exist, wherein the organic acid from an alcoholic fermentation is selected from the group consisting of wine vinegar, apple cider vinegar, white vinegar and rice vinegar.

2. The method of claim 1, wherein the animal cartilage is bovine and/or porcine cartilage.

3. The method of claim 1, wherein the organic acid is apple cider vinegar.

4. The method of claim 1, wherein the enzymatic hydrolysate of animal cartilage protein has a degree of hydrolysis between 8% and 30%.

5. The method of claim 4, wherein the degree of hydrolysis is 20%.

6. The method of claim 1, wherein the enzymatic hydrolysate of animal cartilage protein has an average molecular weight less than or equal to 20,000 Daltons.

7. The method of claim 1, wherein the enzymatic hydrolysate of animal cartilage protein is in a concentration of between 300 g/L and 1,000 g/L.

8. The method of claim 7, wherein the attractant composition is added to a container and the container is hung in the field.

9. The method of claim 1, wherein the organic acid is in a concentration of between 200 g/L and 600 g/L.

10. The method of claim 9, wherein the attractant composition is added to a container and the container is hung in the field.

11. The method of claim 1, wherein the enzymatic hydrolysate of animal cartilage protein is in a concentration of 680 g/L and the organic acid is in a concentration of 340 g/L.

12. The method of claim 11, wherein the attractant composition is added to a container and the container is hung in the field.

13. The method of claim 1, wherein the composition contains 2% by weight of acetic acid, relative to the total weight of the composition.

14. The method of claim 1, wherein the composition contains 7% by weight of enzymatic hydrolysate of animal cartilage protein, relative to the total weight of the composition.

15. The method of claim 1, which further comprises a preservative.

16. The method of claim 1, which further comprises an agent to reduce evaporation of the attractant composition.

17. The method of claim 1, wherein the attractant composition is added to a container and the container is hung in the field.

18. The method of claim 17, wherein the container contains a membrane for impregnating with the attractant composition.

19. The method of claim 17, wherein the container is a trap for capturing the flies.

20. The method of claim 1, wherein the attractant composition comprises 66% of the enzymatic hydrolysate of animal cartilage protein and 34% of the organic acid.

* * * * *